(12) United States Patent
Kim et al.

(10) Patent No.: US 10,377,864 B2
(45) Date of Patent: Aug. 13, 2019

(54) PLASTICIZER COMPOSITION, RESIN COMPOSITION AND METHOD FOR PREPARING THEREOF

(71) Applicant: LG CHEM, LTD., Seoul (KR)

(72) Inventors: Hyun Kyu Kim, Daejeon (KR); Mi Yeon Lee, Daejeon (KR); Jeong Ju Moon, Daejeon (KR); Joo Ho Kim, Daejeon (KR); Seok Ho Jeong, Daejeon (KR)

(73) Assignee: LG Chem, Ltd., Seoul (KR)

( * ) Notice: Subject to any disclaimer, the term of this patent is extended or adjusted under 35 U.S.C. 154(b) by 6 days.

(21) Appl. No.: 15/533,264

(22) PCT Filed: Apr. 6, 2016

(86) PCT No.: PCT/KR2016/003581
§ 371 (c)(1),
(2) Date: Jun. 5, 2017

(87) PCT Pub. No.: WO2016/163744
PCT Pub. Date: Oct. 13, 2016

(65) Prior Publication Data
US 2017/0369656 A1    Dec. 28, 2017

(30) Foreign Application Priority Data

Apr. 6, 2015 (KR) .............. 10-2015-0048546
May 15, 2015 (KR) .............. 10-2015-0068279
Mar. 31, 2016 (KR) .............. 10-2016-0039672

(51) Int. Cl.
*C08J 3/18* (2006.01)
*C07C 55/22* (2006.01)
(Continued)

(52) U.S. Cl.
CPC ............ *C08J 3/18* (2013.01); *C07C 55/22* (2013.01); *C07C 63/24* (2013.01); *C08K 5/092* (2013.01);
(Continued)

(58) Field of Classification Search
CPC .. C08J 3/18; C08K 5/0016; C08K 5/10; C08K 5/09
(Continued)

(56) References Cited

U.S. PATENT DOCUMENTS 4,464,502 A * 8/1984 Jacobs .................. C08K 3/22
524/411
5,021,490 A * 6/1991 Vyvoda ............ C08F 299/0478
524/140
(Continued)

FOREIGN PATENT DOCUMENTS

CN    1696189 A    11/2005
CN    101085736 A    12/2007
(Continued)

OTHER PUBLICATIONS

Database WPI: "Celestite powder of nano-modified chlorosulfonated polyethylene rubber sealing pad comprises chlorosulfonated polyethylene rubber, epichlorohydrin rubber, acyloxy (acyloxy dioctyl phosphate) titanate, and modified ash trees", XP002778152, Thomson Scientific, Mar. 27, 2013 (Corresponds to CN102993584A).

*Primary Examiner* — Jane L Stanley
(74) *Attorney, Agent, or Firm* — Dentons US LLP (57) ABSTRACT

The present invention relates to a plasticizer composition, a resin composition and a method for preparing thereof. The present invention can provide a plasticizer composition, which can improve properties required to the plasticizer composition contained in a vinyl chloride-based resin composition, such as plasticizing efficiency, volatile loss, and migration resistance, to a level equal to or better than the existing plasticizer composition, and a resin composition comprising thereof.

13 Claims, 6 Drawing Sheets

| Eval. | 0 | 0.5 | 1.0 | 1.5 | 2.0 | 2.5 | 3.0 |
|---|---|---|---|---|---|---|---|
| standard | | | | | | | |

(51) Int. Cl.
*C07C 63/24* (2006.01)
*C08K 5/092* (2006.01)
*C08K 5/134* (2006.01)
*C08K 5/11* (2006.01)
*C08K 5/12* (2006.01)
*C08K 5/1515* (2006.01)

(52) U.S. Cl.
CPC .............. *C08K 5/11* (2013.01); *C08K 5/12* (2013.01); *C08K 5/134* (2013.01); *C08K 5/1515* (2013.01)

(58) Field of Classification Search
USPC ........................................................ 524/292
See application file for complete search history.

(56) References Cited

U.S. PATENT DOCUMENTS

| | | | | |
|---|---|---|---|---|
| 5,319,028 A | * | 6/1994 | Nakamura | C08F 265/04 525/227 |
| 6,730,741 B1 | * | 5/2004 | Honda | C08L 27/06 525/228 |
| 9,534,104 B2 | * | 1/2017 | Naert | C09D 127/06 |
| 9,546,259 B2 | * | 1/2017 | Colle | C07B 41/12 |
| 2004/0097625 A1 | * | 5/2004 | Bodart | C08K 5/0008 524/315 |
| 2004/0143068 A1 | * | 7/2004 | Honda | C08F 259/08 525/199 |
| 2005/0020718 A1 | * | 1/2005 | Gosse | C08K 5/12 523/105 |
| 2007/0287781 A1 | | 12/2007 | Grass et al. | |
| 2010/0305250 A1 | * | 12/2010 | Colle | C08K 5/0016 524/112 |
| 2013/0225737 A1 | * | 8/2013 | Gosse | C08K 5/12 524/285 |
| 2014/0315021 A1 | | 10/2014 | Naert et al. | |
| 2017/0081501 A1 | * | 3/2017 | Kim | C08J 5/00 |
| 2018/0022893 A1 | * | 1/2018 | Kim | C08K 5/1515 |
| 2018/0066124 A1 | * | 3/2018 | Kim | C08K 5/0016 |

FOREIGN PATENT DOCUMENTS

| | | |
|---|---|---|
| CN | 102993584 A | 3/2013 |
| CN | 102995451 A | 3/2013 |
| CN | 103131145 A | 6/2013 |
| JP | 2012255104 A | 12/2012 |

* cited by examiner

| | DINIP+TBC +ESO 6:3:1 | DINIP+TBC +ESO 5:3:2 | DINIP+TBC +ESO 4:3:3 | DINIP+TBC +eFAME 6:3:1 | DINIP+TBC 7:3 |
|---|---|---|---|---|---|
| 3 min | | | | | |
| 4 min | | | | | |
| 5 min | | | | | |
| 6 min | | | | | |
| 7 min | | | | | |
| 8 min | | | | | |

[FIG. 7]

| | DINIP+TBC +ESO 6:3:1 | DINIP+TBC +ESO 5:3:2 | DINIP+TBC +ESO 4:3:3 | DINIP+TBC +eFAME 6:3:1 | DINIP+TBC 7:3 |
|---|---|---|---|---|---|
| 0 hr | | | | | |
| 24 hr | | | | | |
| ΔE | 41.80 | 41.52 | 41.25 | 55.45 | 57.42 |

PLASTICIZER COMPOSITION, RESIN COMPOSITION AND METHOD FOR PREPARING THEREOF

CROSS-REFERENCE(S) TO RELATED APPLICATION

This application is a National Stage Application of International Application No. PCT/KR2016/003581, filed Apr. 6, 2016, and claims the benefit of Korean Patent Application No. 10-2015-0048546, filed May 15, 2015, and Korean Patent Application No. 10-2015-0068279, filed Sep. 3, 2015, Korean Patent Application No. 10-2016-0039672, filed Mar. 31, 2016, contents of which are incorporated herein by reference in their entirety for all purposes as if fully set forth below.

FIELD OF THE INVENTION

Technical Field

The present invention relates to a plasticizer composition, a resin composition and a method for preparing thereof.

Background Art

In general, a plasticizer is composed of ester formed by reaction of alcohol with polycarboxylic acid such as phthalic acid and adipic acid. Further, in consideration of domestic and foreign regulations of harmful phthalate-based plasticizers, studies for a plasticizer composition, which can replace the phthalate-based plasticizer such as terephthalate-based, adipate-based, and other polymer-based plasticizer, are going on.

Meanwhile, in consideration of the required properties such as migration, volatile loss, plasticizing efficiency and the like, which are required in the businesses of a flooring material, a water play sheet and a film as well as a compound business requiring high heat resistance and low volatile loss as a major property, it is needed to use a proper plasticizer. In the case of a PCV compound for a flooring material, a film, a calendaring sheet and a wire or a cable, additives such as a plasticizer, a stabilizer, a pigment and the like are mixed to PVC resin according to characteristics required in corresponding standards such as tensile strength, elongation rate, plasticizing efficiency, volatile loss, migration, tensile retention and elongation retention.

Currently, among plasticizer products, some phthalate products represented by dioctyl phthalate have harmfulness to a human body, and therefore, environment regulation is conducted in various product families. This trend expands development and use of environmental-friendly plasticizers, and circularly expands environmental friendly plasticizer market area in more diverse products and businesses. Considering the market trend, development of a new environmental-friendly product having quality equal to or better than the phthalate thereby replacing the phthalate is needed.

Accordingly, studies for securing a vinyl chloride-based resin composition, which is free from environmental problems and has excellent quality by developing a new environment-friendly plasticizer composition product having better properties than the existing phthalate and commercialized products, are going on.

DETAILED DESCRIPTION OF THE INVENTION

Technical Problem

Accordingly, the present inventors had been continuing research on a plasticizer, and completed the present invention after finding a plasticizer composition, which can improve bad properties caused by structural limits.

Namely, in order to solve the above problems, one object of the present invention is to provide a plasticizer, which can improve properties such as plasticizing efficiency. migration, gelling and the like required for sheet formulation when the composition is used as a plasticizer of a resin composition, a method for preparing thereof, and a resin composition comprising the same.

Technical Solution

In order to accomplish the objects described above, according to one embodiment of the present invention, provided is a plasticizer composition comprising: an isophthalate-based material; and a citrate-based material, wherein weight ratio of the isophthalate-based material and the citrate-based material is 99:1 to 1:99.

The weight ratio of the isophthalate-based material and the citrate-based material may be 95:5 to 50:50.

The weight ratio of the isophthalate-based material and the citrate-based material may be 95:5 to 60:40.

The isophthalate-based material may be at least one compound selected from the group consisting of di(2-ethyl hexyl) isophthalate (DEHIP or DOIP) and diisononyl isophthalate (DINIP).

The citrate-based material may comprise any one selected from the group consisting of a hybrid alkyl-substituted citrate-based material of carbon number 4 to 9 and non-hybrid alkyl-substituted citrate-based material of carbon number 4 to 9.

The citrate-based material may be a non-hybrid alkyl-substituted citrate-based material of carbon number 4 to 9, and the alkyl group of carbon number 4 to 9 of the citrate-based material is a linear chain or a branched chain.

The plasticizer composition may further comprise epoxidized oil or epoxidized fatty acid alkyl ester.

The epoxidized oil may comprise at least one selected from the group consisting of epoxidized soybean oil, epoxidized castor oil, epoxidized linseed oil, epoxidized palm oil, epoxidized stearic acid, epoxidized oleic acid, epoxidized tall oil and epoxidized linoleic acid.

In order to accomplish the objects described above, according to another embodiment of the present invention, provided is a method for preparing the plasticizer composition, which comprises: a step of preparing the isophthalate-based material and the citrate-based material; and a step of obtaining the plasticizer composition by blending the isophthalate-based material and the citrate-based material at weigh ratio of 99:1 to 1:99.

The method may further comprise a step of mixing the epoxidized oil in an amount of 1 part by weight to 100 parts by weight, based on 100 parts by weight of a mixture of the isophthalate-based material and the citrate-based material, after the step of obtaining the plasticizer composition by blending.

In order to accomplish the objects described above, according to further another embodiment of the present invention, provided is a resin composition comprising resin 100 parts by weight; and the plasticizer composition described above 5 parts by weight to 150 parts by weight.

The resin may be at least one selected from the group consisting of ethylene vinyl acetate, polyethylene, polypropylene, polyvinyl chloride, polystyrene, polyurethane and thermoplastic elastomer.

The resin composition may be applied for manufacturing at least one material selected from the group consisting of a wire, a flooring material, an interior material for a vehicle, a film, a sheet, wallpaper and a tube.

Advantageous Effect

The plasticizer composition according to one embodiment of the present invention can improve properties such as plasticizing efficiency, tensile strength and elongation rate, and also can provide excellent properties in items such as migration resistance and volatile loss when used for a resin composition.

BEST MODE FOR CARRYING OUT THE INVENTION

EXAMPLE

Hereinafter, the preferred embodiment of the present invention will be described in detail based on examples. However, the embodiments of the present invention may be modified in various ways, and the scope of the present invention should not be interpreted as being limited to the examples. The embodiments of the present invention are provided just for explaining the present invention more perfectly to those having ordinary skill in the art.

Preparation Example 1

Preparation of Diisononyl Isophthalate (DINIP)

Purified isophthalic acid (PIA) 498.0 g and isononyl alcohol (INA) 1298.3 g (molar ratio of PIA and INA was 1.0:3.0), and a titanium catalyst (tetra isopropyl titanate (TIPT)) as a catalyst 1.54 g (0.31 part by weight, based on PIA 100 parts by weight) were put into a 4-neck 3-liter reactor equipped with a cooler, a water stripper, a condenser, a decanter, a reflux pump, a temperature controller, a stirrer and the like, and then slowly heated up to about 170° C. Product water begun to be formed around 170° C. Esterification reaction was conducted for about 4.5 hour at a reaction temperature of about 220° C. under atmospheric pressure while continuously inserting nitrogen gas, and the reaction was completed when acid value reached 0.01.

After the reaction was completed, distillation extraction was conducted for 0.5 hour to 4 hours under reduced pressure to remove unreacted raw materials. In order to remove the unreacted raw materials below a certain content level, steam extraction was conducted using steam for 0.5 hour to 3 hours under reduced pressure, and the reacted solution was cooled to a temperature of about 90° C. and then neutralized using alkali solution. In addition, washing may be conducted, and then the reacted solution was dehydrated to remove moisture. Media were inserted to the dehydrated reacted solution followed by stirring thereof for a period of time, and then the solution was filtered to finally obtain diisononyl isophthalate 1243.3 g (Yield: 99.0%).

Preparation Example 2

Preparation of Diethyl Hexyl Isophthalate (DOIP)

The procedure of Preparation Example 1 was repeated to conduct reaction except for using ethyl hexyl alcohol instead of isononyl alcohol, and diethyl hexyl isophthalate 1148.1 g (Yield: 98%) was finally obtained.

Preparation Example 3

Preparation of TBC

Using citric acid 384 g and butanol 580 g as a raw material of reaction, tributyl citrate 706 g (Yield: 98%) was finally obtained.

Preparation Example 4

Preparation of TOC

Using citric acid 384 g and 2-ethyl hexanol 1014 g as a raw material of reaction, tri-2-ethylhexyl citrate 1029 g (Yield: 98%) was finally obtained.

Plasticizer compositions of Examples 1 to 4 were prepared by mixing the materials prepared in Preparation Examples 1 to 4 as shown in the following Tables 1 to 3, and evaluation of properties of the plasticizer compositions were conducted according to the following test items.

TABLE 1

|  | Isophthalate-based material | Citrate-based material | Weight ratio for mixing |
| --- | --- | --- | --- |
| Example 1-1 | Preparation Example 1 (DINIP) | Preparation Example 3 (TBC) | 9:1 |
| Example 1-2 |  |  | 7:3 |
| Example 1-3 |  |  | 5:5 |
| Example 2-1 |  | Preparation Example 4 (TOC) | 9:1 |
| Example 2-2 |  |  | 7:3 |
| Example 2-3 |  |  | 5:5 |

TABLE 2

|  | Isophthalate-based material | Citrate-based material | Weight ratio for mixing |
| --- | --- | --- | --- |
| Example 3-1 | Preparation Example 2 (DOIP) | Preparation Example 3 (TBC) | 95:5 |
| Example 3-2 |  |  | 8:2 |
| Example 3-3 |  |  | 5:5 |
| Example 3-4 |  |  | 1:9 |
| Example 3-5 |  | Preparation Example 4 (TOC) | 7:3 |

TABLE 3

| | Isophthalate-based material | Citrate-based material | Additives | Weight ratio for mixing |
|---|---|---|---|---|
| Example 4-1 | Preparation Example 1 (DINIP) | Preparation Example 3 (TBC) | ESO | 6:3:1 |
| Example 4-2 | | | ESO | 5:3:2 |
| Example 4-3 | | | ESO | 4:3:3 |
| Example 4-4 | | | eFAME | 6:3:1 |

<Test Item>

Measuring Hardness

Using ASTM D2240, shore hardness at 25° C., 3T 10 s was measured.

Measuring Tensile Strength

According to ASTM D638 method, a test specimen was pulled using a tester U.T.M (Manufacturer; Instron, Model No.; 4466) at cross head speed of 200 mm/min (1 T), and then a point when the test specimen was broken was measured. Tensile strength was calculated as follows:

Tensile Strength ($kgf/cm^2$) =Load value (kgf) / Thickness (cm)×Width (cm)

Measuring Elongation Rate

According to ASTM D638 method, a test specimen was pulled using a tester U.T.M at cross head speed of 200 mm/min (1 T), and then a point when the test specimen was broken was measured. Elongation rate was calculated as follows:

Elongation Rate (%)=[Length after elongation/Initial length]×100

Measuring Migration Loss

A test specimen having thickness of 2 mm or thicker was obtained according to KSM-3156, and PS Plates were attached to both sides of the test specimen followed by adding a load of 1 $kgf/cm^2$ thereto. The test specimen was left in a hot air circulation oven (80° C.) for 72 hours, taken out therefrom, and then cooled at an ordinary temperature for 4 hours. Then, the PS plates attached to both sides of the test specimen were removed, weight before and after left in the oven was measured, and then migration loss was calculated according to the following formula.

Migration Loss (%)=[(Initial weight of test specimen at ordinary temperature−Weight of test specimen after left in oven)/Initial weight of test specimen at ordinary temperature]×100

Measuring Volatile Loss

The prepared test specimen was processed at 80° C. for 72 hours, weight of the test specimen was measured, and then volatile loss was calculated according to the following formula.

Volatile Loss (%)=[(Initial weight of test specimen−Weight of test specimen after processed)/Initial weight of test specimen]×100

Measuring Heat Resistance

According to a method for measuring volatile loss, discoloration degree of an initial test specimen and a test specimen after volatile loss test was measured. The measured value was determined by difference in E value against L, a and b values obtained by using a colorimeter.

Test Example 1

DINIP and TBC-Mixed Plasticizer Composition

The DINIP and the TBC were mixed at mixing ratio of Examples 1-1 to 1-3 as shown in the Table 1 to obtain mixed plasticizer compositions, and the compositions were used as a test specimen.

Referring to ASTM D638, the test specimen was manufactured by mixing the mixed plasticizer composition 40 parts by weight, a stabilizer (BZ153T) 3 parts by weight and $TiO_2$ 1 part by weight to PVC 100 part by weight in a 3L super mixer under conditions of 98° C. and 700 rpm, processed using a roll mil at 160° C. for 4 min to make a 5 mm sheet, and then pressed at 180° C. for 2.5 min at low pressure and then 2 min at high pressure. The results of evaluating properties of each test specimen against the above items were shown in the following Table 4.

TABLE 4

| | Plasticizer | Hardness (Shore "A") | Tensile Strength ($kg/cm^2$) | Elongation Rate (%) | Migration Loss (%) | Volatile Loss (%) | Stress test (168 hours) |
|---|---|---|---|---|---|---|---|
| Example 1-1 | 9:1 | 90.1 | 226.80 | 298.11 | 1.38 | 0.94 | 1.5 |
| Example 1-2 | 7:3 | 88.6 | 223.02 | 292.42 | 1.40 | 1.61 | 1.0 |
| Example 1-3 | 5:5 | 87.2 | 221.8 | 295.6 | 1.56 | 1.85 | 0.5 |
| Comparative Example 1-1 | DINP | 90.6 | 217.95 | 288.21 | 1.42 | 0.95 | 0.5 |
| Comparative Example 1-2 | DOTP | 93.7 | 225.3 | 280.20 | 1.30 | 0.51 | 2.5 |
| Comparative Example 1-3 | DINIP | 93.1 | 223.63 | 302.16 | 1.35 | 0.58 | 2 |

*Hardness: 3 T, 10 s
*Tensile Strength and Elongation Rate: 1 T, 200 mm/min
*Migration Loss: 80° C., 1 T, 1 $kgf/cm^2$, 72 hr
*Volatile Loss: 80° C., 72 hr
*Stress Test: 23° C., 168 hr As shown in the Table 4, the existing plasticizer product broadly sold in the market, which can be used in the similar business with the plasticizer composition of the present invention, may be DINP, DOTP or DINIP and the like. When comparing Comparative Examples 1-1 to 1-3 using the product with Examples 1-1 to 1-3, it can be found that Comparative Example 1-3 not mixing the citrate-based material had higher hardness than Examples, and therefore, plasticizing efficiency was decreased, and stress migration was bad. Furthermore, when comparing the plasticizer product having excellent performance like DINP with Examples, it can be confirmed that all properties including absorption speed, tensile strength, elongation rate and stress migration resistance are equal to or better than Examples. Accordingly, it was confirmed that the plasticizer composition of the present invention can improve bad properties of the existing plasticizer product and also can obtain an advantage of being free from environmental problems.

Test Example 2

DINIP and TOC-Mixed Plasticizer Composition

The DOIP and the TOC were mixed at mixing ratio of Examples 2-1 to 2-3 as shown in the Table 1 to obtain mixed plasticizer compositions, and the compositions were used as a test specimen. Manufacture of a test specimen and evaluation of property were identically conducted as described in Test Example 1, and the results were shown in the following Table 5.

TABLE 5

| | Plasticizer | Hardness (Shore "A") | Tensile Strength (kg/cm²) | Elongation Rate (%) | Migration Loss (%) | Volatile Loss (%) | Stress test (24 hours) |
|---|---|---|---|---|---|---|---|
| Example 2-1 | 9:1 | 92.9 | 232.13 | 309.27 | 1.33 | 0.59 | 1.5 |
| Example 2-2 | 7:3 | 92.4 | 235.00 | 320.46 | 1.02 | 0.50 | 1.0 |
| Example 2-3 | 5:5 | 91.8 | 241.3 | 335.6 | 0.86 | 0.47 | 1.0 |
| Comparative Example 1-1 | DINP | 90.6 | 217.95 | 288.21 | 1.42 | 0.95 | 0.5 |
| Comparative Example 1-2 | DOTP | 93.7 | 225.3 | 280.20 | 1.30 | 0.51 | 2.5 |
| Comparative Example 1-3 | DINIP | 93.1 | 223.63 | 302.16 | 1.35 | 0.58 | 2 |

As shown in the Table 5, the existing plasticizer product broadly sold in the market, which can be used in the similar business with the plasticizer composition of the present invention, may be DINP, DOTP or DINIP and the like. When comparing Comparative Examples 1-1 to 1-3 using the product with Examples 2-1 to 2-3, it can be found that Comparative Example 1-3 not mixing the citrate-based material had equal hardness to Examples, and therefore, plasticizing efficiency was not different but stress migration, or tensile strength and elongation rate were bad. Furthermore, when comparing the plasticizer product having excellent performance like DINP with Examples, it can be confirmed that all properties including absorption speed, tensile strength, elongation rate and stress migration resistance are equal to or better than Examples. Accordingly, it was confirmed that the plasticizer composition of the present invention can improve bad properties of the existing plasticizer product and also can obtain an advantage of being free from environmental problems.

Test Example 3

DOIP and TBC-Mixed Plasticizer Composition

Evaluation of Basic Property

The DOIP and the TBC or the TOC were mixed at mixing ratio of Examples 3-1 to 3-5 as shown in the Table 2 to obtain mixed plasticizer compositions, and the compositions were used as a test specimen.

Referring to ASTM D638, the test specimen was manufactured by mixing the mixed plasticizer composition 40 parts by weight and a stabilizer (BZ153T) 3 parts by weight to PVC 100 part by weight in a 3L super mixer under conditions of 98° C. and 700 rpm, processed using a roll mil at 160° C. for 4 min to make a 5 mm sheet, and then pressed at 180° C. for 2.5 min at low pressure and then 2 min at high pressure. The results of evaluating properties of each test specimen against the above-mentioned test items were shown in the following Table 6.

TABLE 6

| | Plasticizer | Hardness (Shore "A") | Tensile Strength (kg/cm²) | Elongation Rate (%) | Migration Loss (%) | Volatile Loss (%) |
|---|---|---|---|---|---|---|
| Example 3-1 | 95:5 | 89.0 | 227.4 | 294.3 | 1.73 | 1.04 |
| Example 3-2 | 8:2 | 88.0 | 224.9 | 291.2 | 1.65 | 1.68 |
| Example 3-3 | 5:5 | 86.3 | 211.9 | 276.5 | 1.52 | 1.99 |
| Example 3-4 | 1:9 | 85.0 | 198.5 | 267.8 | 1.53 | 3.17 |
| Example 3-5 | 7:3 | 89.5 | 231.8 | 300.4 | 1.31 | 0.68 |
| Comparative Example 3-1 | DOTP | 91.0 | 222.4 | 292.5 | 1.84 | 1.57 |
| Comparative Example 3-2 | DOIP | 89.8 | 226.4 | 299.6 | 1.72 | 1.22 |

*Hardness: 3 T, 10 s
*Tensile Strength and Elongation Rate: 1 T, 200 mm/min
*Migration Loss: 80° C., 1 T, 1 kgf/cm², 72 hr
*Volatile Loss: 80° C., 72 hr As shown in the Table 6, the existing plasticizer product broadly sold in the market, which can be used in the similar business with the plasticizer composition of the present invention, may be DOTP or DOIP and the like. When comparing Comparative Examples 3-1 and 3-2 using the product with Examples 3-1 to 3-5, it can be found that Comparative Example 3-2 not mixing the citrate-based material had higher hardness than Examples, and therefore, plasticizing efficiency was decreased, and stress migration was different. Namely, it can be confirmed that, in the case of adding the citrate-based material to the plasticizer composition of the DOIP, plasticizing efficiency can be enhanced and also migration loss can be reduced.

Stress Test

A stress test was conducted using the above test specimens according to the above-mentioned test items, and measured after 24 hours, 72 hours and 168 hours, respectively, and the results were shown in the following Table 7 and FIGS. 1 to 4.

TABLE 7

|  | 24 hours | 72 hours | 168 hours |
| --- | --- | --- | --- |
| Example 3-1 | 0.5 | 1.0 | 1.5 |
| Example 3-2 | 0 | 0.5 | 1.0 |
| Example 3-3 | 0 | 0 | 0.5 |
| Example 3-4 | 0 | 0 | 0 |
| Example 3-5 | 0 | 1.0 | 1.5 |
| Comparative Example 3-1 | 0.5 | 1.5 | 1.5 |
| Comparative Example 3-2 | 0.5 | 1.0 | 1.5 |

As shown in the Table 7, it can be confirmed that, in the cases of Comparative Examples 3-1 and 3-2, migration was ongoing after only 24 hours, and it can be confirmed that, in the cases of Examples, migration was ongoing a little until 72 hours after. Namely, it can be confirmed that, in the case of adding the citrate, property improvement about stress migration can be achieved.

Test Example 4

DOIP, TBC and Epoxidized Oil-Mixed Plasticizer Composition

The DINIP, the TBC and ESO or eFAME were mixed at mixing ratio of Examples 4-1 to 4-4 as shown in the Table 3 to obtain mixed plasticizer compositions, and the compositions were used as a test specimen. The test specimen was manufactured by the same method with Test Example 1 except for adding the mixed plasticizer composition 30 parts by weight during sheet formulation and using the titanium dioxide ($TiO_2$, KA-100) in an amount of 0.5 part by weight.

Further, evaluation was divided into evaluation of heat resistance at high temperature and evaluation of heat resistance for a long time. The evaluation of heat resistance at high temperature was conducted in Mathis oven at 180° C. and 220° C., respectively, and the evaluation of heat resistance for a long time was conducted in Gear oven. The results were shown in FIGS. 5 to 7.

Figure 1:
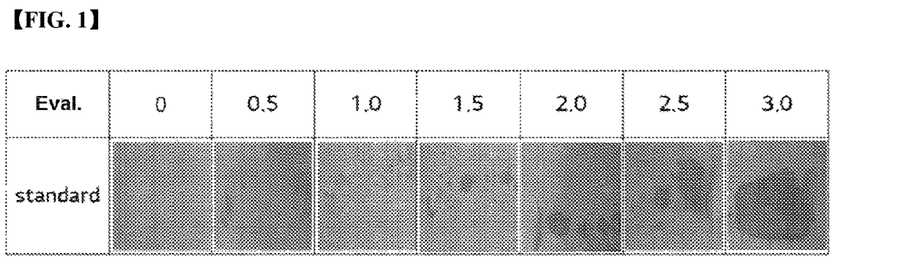
FIG. 1 represents evaluation standards for a stress test depending on state of a test.
Figure 2:
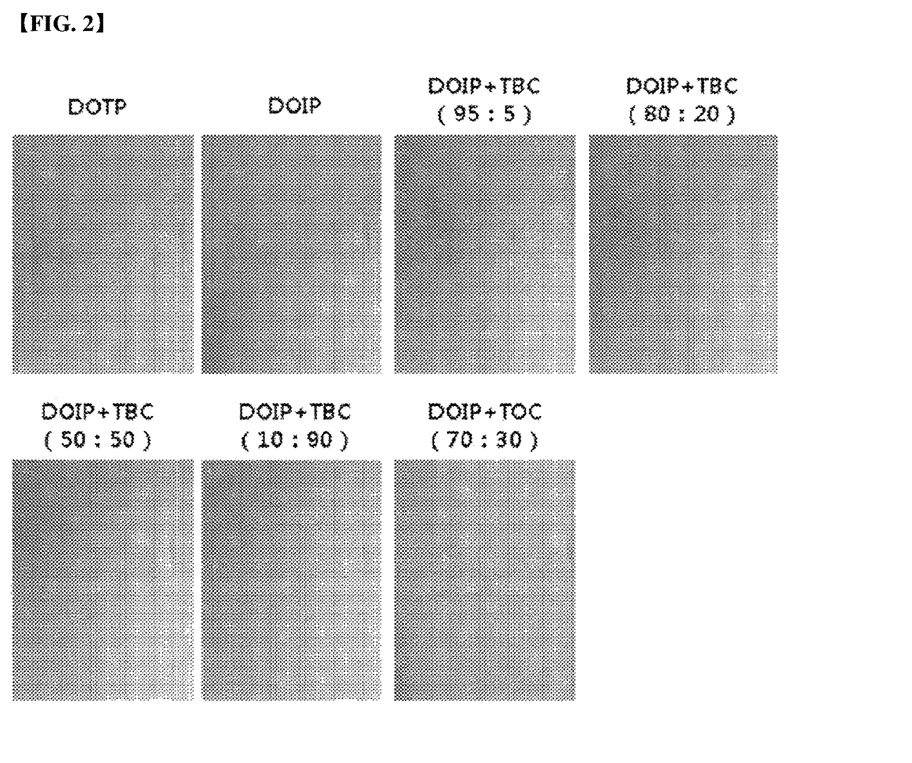
FIG. 2 represents the result of a stress test (24 hours) depending on mixing ratio of a plasticizer composition.
Figure 3:
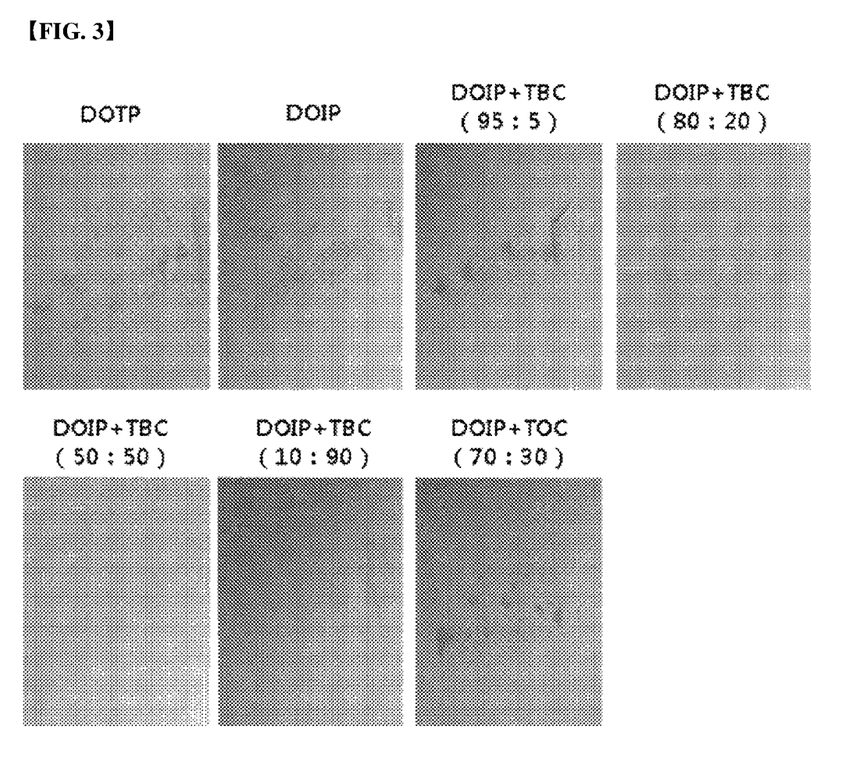
FIG. 3 represents the result of a stress test (72 hours) depending on mixing ratio of a plasticizer composition.
Figure 4:
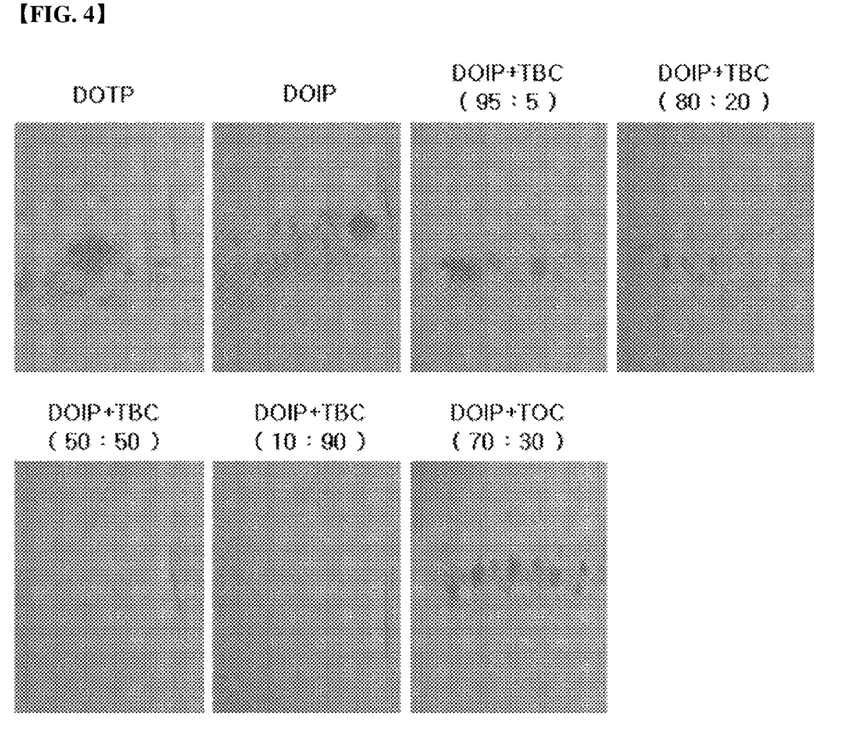
FIG. 4 represents the result of a stress test (168 hours) depending on mixing ratio of a plasticizer composition.
Figure 5:
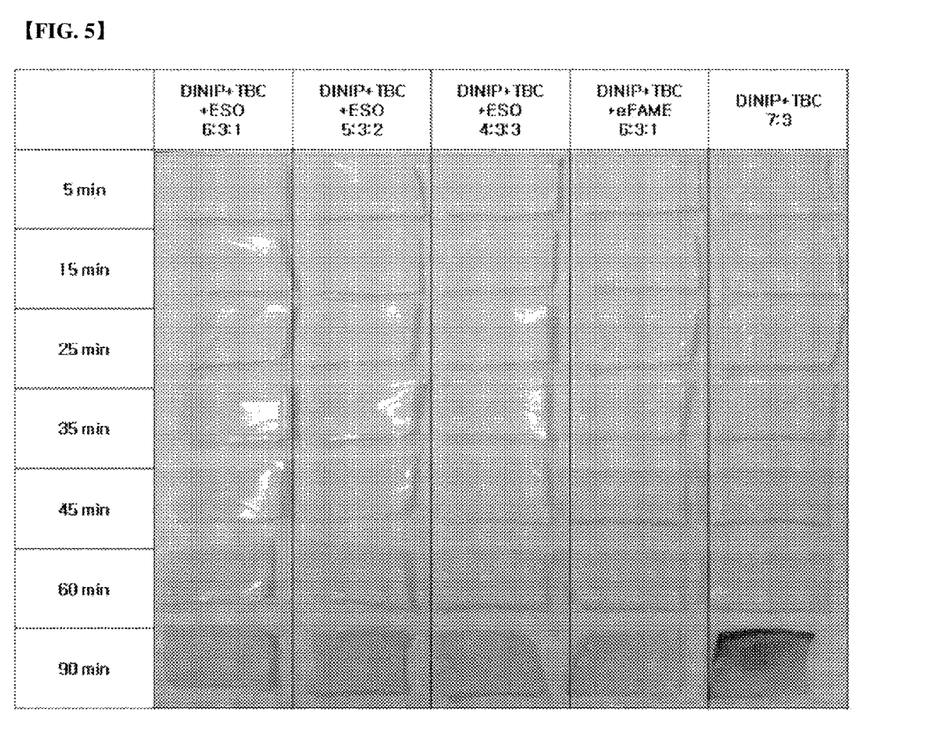
FIG. 5 represents the result of evaluation heat resistance at high temperature of 180° C. when adding an additive to a plasticizer composition.
Figure 6:
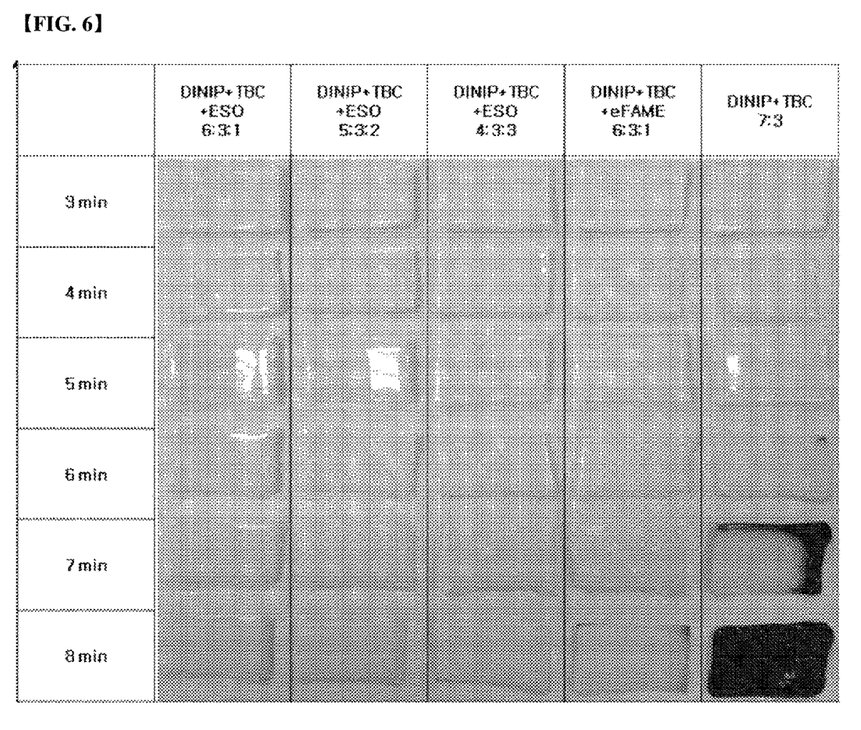
FIG. 6 represents the result of evaluation heat resistance at high temperature of 220° C. when adding an additive to a plasticizer composition.

Referring to FIGS. 5 and 6 about the evaluation of heat resistance at high temperature, in the case of not using the additive in FIG. 5, trace of combustion of a part of the test specimen was can be found after 90 min, and in FIG. 6, it can be found that the test specimen was completely combusted after only 3 min However, it can be confirmed that, in the cases of Examples 4-1 to 4-4 mixed with the additive, the test specimen was remained intact until the test specimen not mixed with the additive had been completely combusted.

Figure 7:
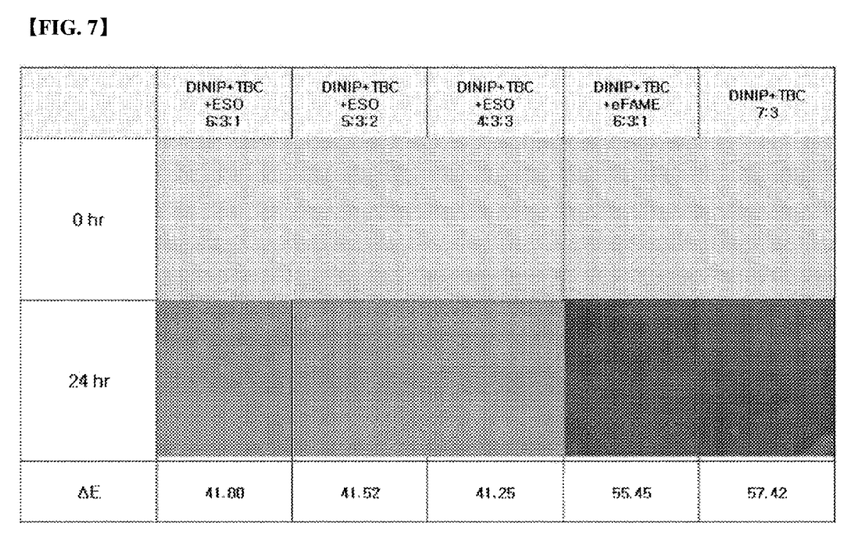
FIG. 7 represents the result of evaluation heat resistance for a long period of 24 hours when adding an additive to a plasticizer composition.

Further, referring to FIG. 7 about evaluation of heat resistance for a long time, in the case of not adding the additive as well as the case of adding the eFAME not the epoxidized oil, there was no effect on improving heat resistance for a long time, but in the case of adding the epoxidized oil, it can be confirmed with naked eyes that the test specimen was not seriously damaged even after the heat resistance evaluation for 24 hours.

Namely, it can be confirmed that, in the case of adding the epoxidized oil such as ESO or the epoxidized fatty acid alkyl ester such as eFAME as an additive, heat resistance can be improved, and in particular, in the case of adding the epoxidized oil, the improvement effect is remarkable.

While the invention has been shown and described with reference to exemplary embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

[Mode for the Invention]

Hereinafter, the present invention will be described in more detail.

First of all, the present invention is technically characterized by providing a plasticizer composition, which can improve bad properties caused by structural limitations.

According to one embodiment of the present invention, a plasticizer composition containing an isophthalate-based material can be provided. Specifically, the isophthalate-based material may be used in an amount within the range of 1 to 99 wt %, 20 to 99 wt %, 40 to 99 wt %, 50 to 95 wt % or 60 to 90 wt %, based on the total weight of the composition.

For example, the isophthalate-based material may be the one having a terminal group independently selected from alkyl groups of carbon number 1 to 12, carbon number 3 to 11, carbon number 4 to 10, carbon number 8 to 10, carbon number 8 to 9, or carbon number 8.

The isophthalate-based material may be at least one compound selected from the group consisting of di(2-ethyl hexyl) isophthalate (DEHIP or DOIP) and diisononyl isophthalate (DINIP).

According to one embodiment of the present invention, the plasticizer composition may further comprise a citrate-based material, and the citrate-based material may comprise at least one compound selected from the group consisting of a hybrid alkyl-substituted citrate-based material of carbon number 4 to 9 and non-hybrid alkyl-substituted citrate-based material of carbon number 4 to 9.

Like this, in the case of a resin manufactured from the plasticizer composition wherein the isophthalate-based compound and the citrate-based material are mixed together, the resin may have better properties such as tensile strength or elongation rate than a resin manufactured from the plasticizer composition comprising only the isophthalate-based compound, and also have better tensile retention and elongation retention, volatile loss, and migration resistance.

For example, the hybrid alkyl-substituted citrate-based material of carbon number 4 to 9 may be citrate having combined substituents of alkyl groups of carbon number 4 and 8 such as 1,2-dibutyl 3-(2-ethyl hexyl) 2-hydroxypropane-1,2,3-tricarboxylate, 1,3-dibutyl 2-(2-ethyl hexyl) 2-hydroxypropane-1,2,3-tricarboxylate, 1-butyl 2,3-bis(2-ethyl hexyl) 2-hydroxypropane-1,2,3-tricarboxylate, or 2-butyl 1,3-bis(2-ethyl hexyl) 2-hydroxypropane-1,2,3-tricarboxylate; citrate having combined substituents of alkyl groups of carbon number 5 and 7 such as 1,2-dipentyl 3-heptyl 2-hydroxypropane-1,2,3-tricarboxylate, 1,3-dipentyl 2-heptyl 2-hydroxypropane-1,2,3-tricarboxylate, 1-pentyl 2,3-diheptyl 2-hydroxypropane-1,2,3-tricarboxylate, or 2-butyl 1,3-diheptyl 2-hydroxypropane-1,2,3-tricarboxylate; or citrate having combined substituents of two alkyl groups of different carbon number selected from 4 to 9, and the alkyl groups may be a linear chain or a branched chain.

In the non-hybrid alkyl-substituted citrate-based material of carbon number 4 to 9, the alkyl groups of carbon number 4 to 9 may be a linear chain or a branched chain. For example, the material may be tributyl citrate (TBC), tripentyl citrate (TPC), trihexyl citrate (THC), triheptyl citrate (THC), trioctyl citrate (TOC), trinonyl citrate (TNC) and the like, and the butyl group to nonyl group may include structural isomers of each, for example, isobutyl group for butyl group, 2-ethyl hexyl group for octyl group and the like.

The non-hybrid alkyl-substituted citrate-based material of carbon number 4 to 9 may be more preferred than the hybrid alkyl-substituted citrate-based material, and tributyl citrate and/or tri(2-ethyl hexyl) citrate may be more frequently used, but not limited thereto.

Meanwhile, like the hybrid or the non-hybrid alkyl-substituted citrate-based material, trialkyl citrate, di-n-alkyl-m-alkyl citrate and the like may be used. If an acetyl group exists in the citrate-based material, properties of a plasticizer, in particular, plasticizing efficiency may be reduced, thereby deteriorating processability and gelling.

In other word, if the citrate-based material is an acetyl citrate-based material wherein hydrogens of hydroxy group except three ester groups are substituted with acetyl groups, reduction in diverse aspects such as marketability, economic feasibility and properties may become a problem due to reduction of plasticizing efficiency, increase of addition amount of the plasticizer to overcome the reduction of plasticizing efficiency thereby rising cost of products.

Herein, in the plasticizer composition, the isophthalate-based material and the citrate-based material may be contained at weight ratio of 99:1 to 1:99, 99:1 to 20:80, 99:1 to 40:60, 99:1 to 50:50, or 99:1 to 60:40, preferably, 95:5 to 50:50, or 90:10 to 60:40.

The plasticizer composition comprises the isophthalate-based material and the citrate-based material, and may further comprise epoxidized oil.

In the case of the mixed plasticizer composition of the isophthalate-based material and the citrate-based material, among various properties, heat resistance may be relatively worse, and this heat resistance can be complemented by containing the epoxidized oil or epoxidized fatty acid alkyl ester more.

The epoxidized oil may be contained in an amount of 1 part by weight to 100 parts by weight, preferably, 1 part by weight to 80 parts by weight, based on 100 parts by weight of the mixture of the isophthalate-based material and the citrate-based material. If the epoxidized oil is contained in the said amount, a compound, a sheet and the like having excellent properties can be manufactured, and properly applied to a calendaring business and the like. If the epoxidized oil is excessively contained, there may be problems that controlling the properties of the plasticizer composition suitable for purpose may be out of scope of control, undesired properties may be excessively improved, or desired properties may be deteriorated.

The epoxidized oil may be, for example, epoxidized soybean oil, epoxidized castor oil, epoxidized linseed oil, epoxidized palm oil, epoxidized stearic acid, epoxidized oleic acid, epoxidized tall oil, epoxidized linoleic acid or a mixture thereof. Preferably, the epoxidized oil may be the epoxidized soybean oil (ESO), the epoxidized linseed oil (ELO) or a mixture thereof, but not limited thereto.

Further, the epoxidized fatty acid alkyl ester may preferably be the one having alkyl group carbon number of 1 to 3.

In the present invention, a method for preparing the plasticizer composition may be a blending method, and for example, the blending method is as follows:

the isophthalate-based material and the citrate-based material are prepared, and the isophthalate-based material and the citrate-based material are blended at weight ratio of 1:99 to 99:1 to manufacture the plasticizer composition.

The isophthalate-based material can be prepared by direct esterification reaction wherein at least one alcohol selected from 2-ethyl hexyl alcohol or isononyl alcohol, and isophthalic acid is reacted.

The direct esterification reaction can be conducted by a step of inserting isophthalic acid to alcohol, adding a catalyst thereto, and then reacting thereof under nitrogen atmosphere; a step of removing unreacted alcohol and then neutralizing unreacted acid; and a step of dehydrating thereof by distillation under reduced pressure and then filtering thereof.

Further, the alcohol used in the blending method may be used in an amount within the range of 150 mol % to 500 mol %, 200 mol % to 400 mol %, 200 mol % to 350 mol %, 250 mol % to 400 mol %, or 270 mol % to 330 mol %, based on the isophthalic acid 100 mol %.

On the other hand, the catalyst used in the blending method may be, for example, at least one selected from the group consisting of acid catalysts such as sulfuric acid, hydrochloric acid, phosphoric acid, nitric acid, p-toluene sulfonic acid, methane sulfonic acid, ethane sulfonic acid, propane sulfonic acid, butane sulfonic acid and alkyl sulfuric acid; metal salts such as aluminum lactate, lithium fluoride, potassium chloride, cesium chloride, calcium chloride, iron chloride and aluminum phosphate; metal oxides such as heteropolyacids; and organic metal such as natural/synthetic zeolite, cation and anion exchange resins, tetra alkyl titanate and its polymer. Specifically, the catalyst may be tetra alkyl titanate.

Amount of the catalyst may vary depending on its kind, and for example, a homogeneous catalyst may be used in an amount within the range of 0.01 wt % to 5 wt %, 0.01 wt % to 3 wt %, 1 wt % to 5 wt % or 2 wt % to 4 wt %, based on total reactant 100 wt %, and a heterogeneous catalyst may be used in an amount within the range of 5 wt % to 200 wt %, 5 wt % to 100 wt %, 20 wt % to 200 wt %, or 20 wt % to 150 wt %, based on total reactant.

At this time, a reaction temperature may be within the range of 180° C. to 280° C., 200° C. to 250° C., or 210° C. to 230° C.

The direct esterification reaction can be used to prepare the above-mentioned hybrid or non-hybrid citrate-based material. In particular, the hybrid citrate-based material can be prepared by the after-mentioned trans-esterification reaction other than the direct esterification reaction. The hybrid citrate-based material can be prepared as a mixed composition at a certain ratio, and the composition ratio of the mixture to be produced can be controlled by controlling content of the alcohol as a reaction material.

The "trans-esterification reaction" used in the present invention means reaction of alcohol and ester wherein R" of the ester is interchanged with R' of the alcohol as shown in the following Reaction Scheme 1:

[Reaction Scheme 1]

According to one embodiment of the present invention, during the trans-esterification reaction, three kinds of ester compositions can be produced by three number of cases, i.e., the case that alkoxide of alcohol attacks carbon of two ester groups (RCOOR") in an ester-based compound; the case that the alkoxide attacks carbon of one ester group (RCOOR") in the ester-based compound; and the case that the reaction does not occur.

Further, the trans-esterification reaction has an advantage of not causing a waste water problem, compared to the esterification reaction between acid and alcohol, and because the reaction can be conducted without a catalyst, problems occurred while using an acid catalyst can be solved.

According to one embodiment of the present invention, the trans-esterification reaction may preferably be conducted under a reaction temperature of 120° C. to 190° C., preferably 135° C. to 180° C., more preferably 141° C. to 179° C. for 10 min to 10 hours, preferably 30 min to 8 hours, more preferably 1 hour to 6 hours. Within the said temperature and time ranges, a mixture having a citrate-based material at a desired composition ratio can be effectively obtained. At this time, the reaction time may be calculated from the time point reached to the reaction temperature after heating a reactant.

The trans-esterification reaction may be conducted under an acid catalyst or a metal catalyst, and in this case, there is an effect of reduction of reaction time.

The acid catalyst may be, for example, sulfuric acid, methane sulfonic acid or p-toluene sulfonic acid and the like, and the metal catalyst may be, for example, an organic metal catalyst, a metal oxide catalyst, a metal salt catalyst or metal itself.

The metal component may be, for example, any one or a mixture of at least two selected from the group consisting of tin, titanium and zirconium.

Further, the method may further comprise a step of removing the unreacted alcohol and by-products of the reaction, for example, the ester-based compound expressed by Formula 3 by distilling thereof after the trans-esterification reaction.

The distillation may be, for example, two-step distillation independently separating the alcohol and the by-products from each other using a difference in boiling point.

As another example, the distillation may be combination distillation. In this case, there is an effect of relatively stably securing an ester-based plasticizer composition at a desired composition ratio. The combination distillation means that butanol and a by-product of reaction are simultaneously distilled.

After mixing the isophthalate-based material and the citrate-based material, the method may further comprise a step of additionally mixing the additive, and the kind and amount of the additive are as mentioned above.

The plasticizer composition manufactured as described above may be used in an amount within the range of 5 parts by weight to 150 parts by weight, 40 parts by weight to 100 parts by weight, or 40 parts by weight to 50 parts by weight, based on 100 parts by weight of a resin selected from ethylene vinyl acetate, polyethylene, polypropylene, polyvinyl chloride, polystyrene, polyurethane and a thermoplastic elastomer, and also can provide a resin composition effective on all of compound formulation, sheet formulation and plastisol formulation.

For example, the plasticizer composition may be applied for manufacturing a wire, a flooring material, an interior material for a vehicle, a film, a sheet, wallpaper or a tube.

Moreover, the vinyl-based thermoplastic resin of Comparative Example 9 manufactured by inserting the metal complex agent in the polymerization step, not the step of manufacturing the particle core, showed higher iron ion concentration but bad whiteness index, yellow index, turbidity and transparency characteristics, compared to the vinyl-based thermoplastic resin of Examples 1 to 11. This means that the iron ions in the second vinyl-based monomer inserted when manufacturing the particle core are not removed and structural defects has been already generated by the iron ions when manufacturing the particle core thereby reducing thermal stability, and the time of inserting the metal complex agent is a major fact of improving thermal stability of the finally manufactured vinyl-based thermoplastic resin.

The invention claimed is:

1. A plasticizer composition comprising:
   an isophthalate-based material; and
   a citrate-based material,
   wherein weight ratio of the isophthalate-based material and the citrate-based material is 95:5 to 50:50, and
   wherein the citrate-based material does not include an acetyl group.

2. The plasticizer composition of claim 1, wherein the weight ratio of the isophthalate-based material and the citrate-based material is 95:5 to 60:40.

3. The plasticizer composition of claim 1, wherein the isophthalate-based material is at least one compound selected from the group consisting of di(2-ethyl hexyl) isophthalate (DEHIP or DOIP) and diisononyl isophthalate (DINIP).

4. The plasticizer composition of claim 1, wherein the citrate-based material comprises any one selected from the group consisting of a hybrid alkyl-substituted citrate-based material of carbon number 4 to 9 and non-hybrid alkyl-substituted citrate-based material of carbon number 4 to 9.

5. The plasticizer composition of claim 1, wherein the citrate-based material is a non-hybrid alkyl-substituted citrate-based material of carbon number 4 to 9, and the alkyl group of carbon number 4 to 9 of the citrate-based material is a linear chain or a branched chain.

6. The plasticizer composition of claim 1, which further comprises an additive comprising epoxidized oil or epoxidized fatty acid alkyl ester.

7. The plasticizer composition of claim 6, wherein the epoxidized oil comprises at least one selected from the group consisting of epoxidized soybean oil, epoxidized castor oil, epoxidized linseed oil, epoxidized palm oil, epoxidized stearic acid, epoxidized oleic acid, epoxidized tall oil and epoxidized linoleic acid.

8. The plasticizer composition of claim 6, wherein the additive is contained in an amount of 1 part by weight to 100 parts by weight, based on 100 parts by weight of a mixture of the isophthalate-based material and the citrate-based material.

9. A method for preparing the plasticizer composition of claim 1, which comprises:
   a step of preparing an isophthalate-based material and a citrate-based material; and
   a step of obtaining a plasticizer composition by blending the isophthalate-based material and the citrate-based material at weigh ratio of 95:5 to 50:50,
   wherein the citrate-based material does not include an acetyl group.

10. The method of claim 9, which further comprises a step of mixing an epoxidized oil in an amount of 1 part by weight to 100 parts by weight, with 100 parts by weight of the mixture of the isophthalate-based material and the citrate-based material, after the step of obtaining a plasticizer composition by blending.

11. A resin composition comprising:
   100 parts by weight of a resin; and
   5 parts by weight to 150 parts by weight of the plasticizer composition of claim 1.

12. The resin composition of claim 11, wherein the resin is at least one selected from the group consisting of ethylene vinyl acetate, polyethylene, polyketone, polypropylene, polyvinyl chloride, polystyrene, polyurethane and thermoplastic elastomer.

13. The resin composition of claim 11, which is a material of at least one product selected from the group consisting of a wire, a flooring material, an interior material for a vehicle, a film, a sheet, wallpaper and a tube.

* * * * *